United States Patent [19]

Tapper et al.

[11] 4,190,056
[45] Feb. 26, 1980

[54] METHOD AND MEANS FOR RECORDING SWEAT GLAND ACTIVITY

[75] Inventors: Robert Tapper, West Los Angeles; Arthur S. Diamond, Ventura; Ajit S. Arora, San Francisco, all of Calif.

[73] Assignee: General Medical Company, Los Angeles, Calif.

[21] Appl. No.: 846,800

[22] Filed: Oct. 31, 1977

[51] Int. Cl.² ................................................ A61B 5/00
[52] U.S. Cl. ........................................ 128/630; 427/1
[58] Field of Search .................. 128/2 W, 630; 427/1; 283/7; 116/114 AM; 422/63, 68, 56

[56] References Cited

U.S. PATENT DOCUMENTS

| | | | |
|---|---|---|---|
| 1,501,841 | 7/1924 | Drummond | 427/1 |
| 2,082,735 | 6/1937 | Heinecke | 41/41 |
| 2,156,880 | 5/1939 | Slomon | 116/114 |
| 2,249,867 | 7/1941 | Snelling | 73/335 |
| 2,299,652 | 10/1942 | Rahn | 41/4 |
| 2,445,586 | 7/1948 | Simons | 117/1 |
| 2,460,073 | 1/1949 | Davis | 252/408 |
| 2,526,938 | 10/1950 | Davis et al. | 252/408 |
| 2,736,114 | 2/1956 | Krueger | 41/4 |
| 3,121,615 | 2/1964 | Price | 23/254 |
| 3,552,929 | 1/1971 | Fields et al. | 23/253 |
| 3,830,195 | 8/1974 | Burleson | 118/31.5 |
| 3,831,552 | 8/1974 | Schmidt et al. | 118/31.5 |
| 3,851,619 | 12/1974 | Cofield et al. | 118/31.5 |
| 3,867,165 | 2/1975 | Williams et al. | 117/0.5 |
| 3,897,749 | 8/1975 | May et al. | 118/31.5 |
| 3,960,632 | 6/1976 | Gaines et al. | 156/245 |
| 4,029,012 | 6/1977 | Smith et al. | 101/368 |

OTHER PUBLICATIONS

*Research Disclosure*, Jul. 1973, "Footprint (G)", 11135, pp. 42-43, Van Krunkelsven.
*Elementary Quantitative Analysis*, 3rd Edition, D. Van Nostrand, 1948, pp. 265 & 273, Willard & Furman.

*Primary Examiner*—Robert W. Michell
*Assistant Examiner*—Thomas J. Wallen

[57] ABSTRACT

Method and apparatus for recording sweat gland activity which provides a pictorial representation thereof by physical contact of an iodide treated skin area with a dry sensitized substrate. In one preferred embodiment, the sensitized substrate comprises a sheet material which has been coated with an aqueous solution containing from 1 to 10 percent by weight of starch and from 2 to 10 percent by weight of a suitable oxidizing agent such as potassium persulfate. Alternately, the dry sensitized substrate comprises a starch-oxidizing agent mixture which has been impregnated into an absorbent base layer. With slight modification of the foregoing embodiment, the present invention also provides a method and apparatus for obtaining inkless fingerprints by forming a sensitized coating in situ on a substrate. For fingerprinting purposes, the sensitized coating is preferably formed from a quick drying starch-oxidizing agent solution including alcohol as a solvent. Accordingly, an aqueous iodide solution is applied to the skin area, and the treated skin area is subsequently contacted with the dry sensitized coating to produce the fingerprint.

99 Claims, 3 Drawing Figures

METHOD AND MEANS FOR RECORDING SWEAT GLAND ACTIVITY

BACKGROUND OF THE INVENTION

This invention relates to a method and means for recording sweat gland activity which provides a dermatoglyph or pictorial representation which is directly proportional to the amount of sweat exuded by the glands. In more detail, the present invention provides a convenient and inexpensive system for producing dermatoglyphs having excellent contrast, clarity and skin pore resolution by effecting a starch-iodine reaction complex on a sensitized substrate.

In the field of clinical testing, the recordation of sweat gland activity has been proposed to quantitatively and qualitatively measure the amount of sweat exuded by the glands. The results of such recordation provide a valuable diagnostic tool which aids in the determination of pathological conditions in the body and in detection of various diseases. See for example, "Dermatoglyphics of Congenital Abnormalities Without Chromosomal Aberrations," Shiono, H. and Kadowaki, J., Clinical Pediatrics, 14:1003–1013, 1975, and "The Value of Ninhydrine Perspiration Test According to Moberg for the Diagnosis of Retroperitoneal Lymph-Node Malignomas", Kruger, H. and Luning, M., Rad.Diagn. 4:609–614. Other diverse applications for dermatoglyphs include their use in the fields of personal identification and forensic science.

The procedures carried out in analysis of dermatoglyphs are well known and do not form part of the present invention. However, there are numerous problems encountered by technicians in connection with the obtaining of dermatoglyphs which afford a clear, resolute and permanent record of the skin surface, pore structure and sweat gland activity. Some prior attempts have been made to produce such recordations, however, these prior attempts involve the use of potentially harmful or toxic chemicals, produce temporary discoloration of the skin surface to be recorded or are slow and time-consuming to administer. Further, because of a low level of sensitivity, some of the prior attempts require the subject to be exposed to a relatively high temperature environment or require physical exertion of the subject to induce an abnormal level of perspiration.

The present invention overcomes the foregoing deficiencies of the prior attempts related to recordation and provides an improved method and means for recording sweat gland activity which achieves an accurate and clear pictorial representation of sweat gland activity.

SUMMARY OF THE INVENTION

The present invention resides in a novel method and means for recording sweat gland activity to obtain a clear resolute image which is directly proportional to the amount of sweat exuded by the glands. Further, the present invention provides a simple, fast and economical method for producing a substantially permanent dermatoglyph having excellent contrast, clarity and skin pore resolution.

Referring to the present invention, in one embodied form the means for recording sweat gland activity includes (i) a sensitized substrate such as a sheet material which has been coated or impregnated with a relatively light colored mixture of starch and a suitable oxidizing agent; and (ii) a colorless iodide solution to be applied to a skin area to be recorded.

Accordingly, the method of the present invention comprises the steps of: providing a dry sensitized substrate which has been coated or impregnated with a light colored mixture of starch and suitable oxidizing agent, treating the skin area to be recorded with a colorless iodide solution, allowing the iodide solution to dry in skin areas where no perspiration exists and to receive moisture where it develops at each gland orifice, and momentarily contacting the treated skin area with the coated or impregnated substrate.

A dermatoglyph is produced immediately, wherein a dark, starch-iodine reaction complex forms only in those areas where even a trace of skin perspiration exists. The resultant dermatoglyph provides both a graphical measurement of sweat gland activity and a pictorial identification of pore structure and pattern.

In one preferred embodiment, the sensitized substrate comprises a sheet material which has been coated with an aqueous solution containing from 1 to 10 percent by weight of a high amylose starch and from 2 to 10 percent by weight of a suitable oxidizing agent such as sodium or potassium persulfate. Alternately, the starch-oxidizing agent mixture can be impregnated into a base substrate rather than coated onto the sheet material. For impregnating purposes, a more absorbent base such as paper is preferred.

With slight modification of the foregoing method and means, the present invention also provides a method and means for obtaining inkless fingerprints by forming a sensitized coating in situ on a substrate. For fingerprinting purposes, the in situ sensitized coating is preferably formed from a quick drying starch-oxidizing solution including alcohol as a solvent. Further, in this embodiment, some moisture is preferably incorporated into the iodide solution to be applied to the skin area so that the fingerprinting method is relatively independent of sweat gland activity. A preferred iodide solution for fingerprinting purposes comprises from about 2 to 25 percent by weight potassium iodide, and from about 75 to 98 percent by weight of a suitable solvent such as glycerol, water, alcohol or mixtures thereof. A preferred coating fluid for forming the in situ sensitized coating comprises from about 1 to 10 percent by weight potato starch, and from about 2 to 10 percent by weight potassium persulfate and the remainder being a suitable solvent such as water, alcohol or mixtures thereof. Further, a light-colored pigment such as calcium carbonate or titanium dioxide or an inert clay can be added to the sensitized coating fluid to improve contrast of the sensitizing fluid when applied to relatively dark colored substrates.

Other objects and advantages will become apparent from the foregoing description taken in conjunction with the accompanying drawings.

DESCRIPTION OF THE PREFERRED EMBODIMENT

The present invention is concerned with an improved method and means for recording sweat gland activity and is especially applicable for providing dermatoglyphs which are sharp, clear and truly representative of sweat gland activity.

In more detail, the present invention concerns a two component recordation means comprising:

(i) a sensitized substrate such as a sheet material which has been coated or impregnated with a relatively light colored mixture of starch and a suitable oxidizing agent; and (ii) a colorless iodide solution to be applied to a skin area to be recorded.

Accordingly, the sensitized substrate colorimetrically reacts with the iodide treated skin area when the treated skin area is contacted with the substrate. A dermatoglyph is produced immediately, wherein a dark, starch-iodine reaction complex forms only in those areas where even a trace of skin perspiration exists. The resultant dermatoglyph provides both a graphical measurement of sweat gland activity and a pictorial identification of pore structure and pattern.

In particular, the present recordation means was developed by intensive evaluation of numerous materials having the following desired characteristics.

The Oxidizing Agent

Soluble iodide ions derived from the iodide solution applied to the skin area are transferred by skin perspiration to the sensitized substrate where the iodide ions are oxidized to elemental iodine by the reaction formula $$2I^- \rightarrow I_2 + 2e^-$$

The reduction potential for reduction of iodine to iodide is 0.535 volts. Thus, in principal, any substance with a reduction potential of more than this amount will be capable of oxidizing the iodide ions to iodine. However, it has been discovered that in accordance with the present invention the selection of an oxidizing agent having a reduction potential above 1.0 is preferred to ensure a reasonably rapid rate of oxidation and to produce an instant development of the dermatoglyph. Further, the oxidizing agent is preferably a water soluble solid, which is odorless, colorless, and commercially available to keep the cost of preparing the sensitized substrate within a reasonable limit. The following table sets forth a number of oxidizing agents in the form of sodium or potassium salts which were selected for evaluation.

TABLE I

| OXIDIZING AGENT | | OXIDATION POTENTIAL (−) E°, VOLTS |
|---|---|---|
| Persulfate | $S_2O_8^{-2}$ | 2.0 |
| Periodate | $IO_4^-$ | 1.7 |
| Hypochlorite | $ClO^-$ | 1.63–0.88[a] |
| Hypobromite | $BrO^-$ | 1.59–0.7[a] |
| Bromate | $BrO_3^-$ | 1.51–0.61[a] |
| Permanganate | $MnO_4^-$ | 1.49 |
| Chlorate | $ClO_3^-$ | 1.46–0.35[a] |
| Perchlorate | $ClO_4^-$ | 1.37–0.17[a] |
| Dichromate | $Cr_2O_7^{-2}$ | 1.33 |
| Iodate | $IO_3^-$ | 1.195–0.26[a] |

TABLE I-continued

| OXIDIZING AGENT | | OXIDATION POTENTIAL (−) E°, VOLTS |
|---|---|---|
| Selenate | $SeO_4^{-2}$ | 1.15 |
| Monopersulfate[a,b] | $HSO_5^-$ | 1.44 |
| Perborate[c] | $H_2BO_4^-$ | 0.68[a] |

[a] variable depending upon pH
[b] Trade name OXONE (from duPont)
[c] perborate being formed by the following reaction:
$Na_2B_4O_7 + 2NaOH + 4H_2O_2 + 11H_2O \rightarrow 4NaBO_2 \cdot H_2O_2 \cdot 3H_2O$

The Starch

The intensity of starch-iodine complex was determined to be dependent upon the amylose content of the starch. Ordinary soluble starches are suitable for purposes of the present invention but have the lowest amylose content. Other starches were found to be higher in amylose content and therefore preferable for iodometric purposes.

Starch is a carbohydrate that is stored by a majority of plants in a manner analogous to the storage of fats by animals. In accordance with the present invention, suitable starch granules are obtained from grains such as rice, corn, potato, wheat, tapioca and mixtures thereof.

The starch molecule consists of straight chains of glucose units joined by an α-1,4-glucosidic linkage (amylose) and branched chains of glucose molecules joined probably through an α-1,6-glucosidic linkage (amylopectin). Because of its two distinctly different types of chains, linear and branched, the starch molecule can be described as a copolymer of amylose and amylopectin.

The reaction between starch and iodine to form a deeply colored substance is governed by several factors which determine the intensity and hue of the resultant complex, as discussed by R. R. Baldwin, R. S. Bear, and R. E. Rundle, in JACS, Vol. 66, pp. 111–115 (1944), "The Relation of Starch-Iodine Absorption Spectra to the Structure of Starch and Starch Components," and Chemistry, June 1976, Vol. 49, No. 5, pp. 17–18, "Research Reporter." These factors include the nature of the starch, that is, the proportion of the amylose (or unbranched) component, and the chain length of the free (or unbranched) portions of the amylopectin fraction.

The color of the starch-iodine complex shifts towards blue, and the intensity of this color increases, as the chain length of the amylose fraction is increased or as the lengths of the unbranched portions of amylopectin are increased. The color of the iodine-stained amylose is therefore blue, and that of amylopectin is purple to red. See for example, F. L. Bates, D. French, and R. E. Rundle, "Amylose and Amylopectin Content of Starches Determined by their Iodine Complex Formation," JACS, Vol. 65, pp. 142–148 (1943).

Most natural starches consist of about 20–25 percent by weight of amylose and 75–80 percent amylopectin. Typical examples of these starches are A. E. Staley's "PFC Corn Starch" and "Confectioners Eclipse G". In contrast, high amylose corn starches, such as A. E. Staley's "Mira-Quik C" and "F4-369," contain as much as 55 percent amylose.

Because these high amylose starches contain approximately twice as much amylose, they can form twice as much of the blue starch-iodine complex, on a weight basis, as the regular starches. Thus, it is possible to obtain the same amount of color with half as much (high amylose) starch.

However, high amylose starches are less soluble in water. They require either cooking under pressure, or the addition of caustic (or both) to effect solution and tend to gel upon cooling unless their concentration is kept relatively low. These factors make high amylose starches somewhat more difficult to use. In some instances, therefore, it might be more desirable to use a larger amount of regular starch than a lesser amount of a high amylose starch.

In accordance with the present invention, three different procedures were developed in order to obtain starch solutions using high amylose starches:

(1) High amylose starch was dissolved in cold water at a relatively high pH level. 2.5 N NaOH solution was generally used for this purpose and the resultant solution of starch had a pH greater than 13.

(2) High amylose starch was boiled in water for a few minutes to a few hours and the pH was then raised by addition of NaOH until a clear solution was obtained. Starch solutions so prepared also had a pH greater than 13.

(3) High amylose starch was boiled in water for several hours and then allowed to cool to room temperature. This gave a jelly like mass which was treated with an oxidizing agent and then the pH was adjusted to 7. This gave a thick starch paste which was used for coating.

The "soluble starches" normally supplied for laboratory use are specially processed materials. They are usually subjected to a cold acid treatment which reduces the molecular weight of the starch and the size of each granule, thereby improving its water solubility. Soluble potato starch is preferred, for iodometry and in the present invention, over soluble corn starch because the latter product contains a small amount of fat which tends to complex with the amylose making it unavailable to enter into the color-forming reaction with iodine.

The Base Substrate

Eight different grades of paper ranging from non-wet strength to high wet strength were selected for evaluation and found suitable for use as the base substrate. These papers are listed in the following table:

TABLE II

| PAPER | DESCRIPTION | COMMENTS |
|---|---|---|
| A | Potlatch 60 lb. | Wet strength poster |
| B | Potlatch 70 lb. | Wet strength poster |
| C | Potlatch 20 lb. | Special Wet strength |
| D | Crane Type 33-91 | Facsimile base |
| E | Crane Type 33-92 | Facsimile base |
| F | Kimberly Clark 411-B4-01 | Alkaline facsimile |
| G | Potlatch 60 wt "Mountie Offset" | Non-wet strength |
| H | Abitibi, D1057 | Saturating base non-wet strength |

Additionally, it was found that suitable substrates also include relatively inert materials such as polymeric films, metallic foils, fabrics and the like.

The Iodide Solution

The skin area to be recorded by means of the dermatographic method of this invention must first be treated with an iodide solution. Sodium iodide, calcium iodide and potassium iodide solutions were found suitable for this purpose. The solutions may be composed of solvents such as water, a lower alcohol, or a mixture thereof. However, because rapid drying is essential to completing the recordation process quickly, a methanol solvent is preferred.

The term "starch-iodide" paper is familiar to most analytical chemists as a material used to detect the presence of iodine in solution. In these iodometric titrations, the presence or absence of iodine, which is detectable in even trace amounts by the appearance of a blue color, can signal the end-point of an oxidation-reduction reaction.

Willard and Furman in a paper entitled "Elementary Quantitative Analysis", 3rd Edition, D. Van Nostrand Co., Inc., New York (1948), pp. 265 and 273, describe the preparation of starch-iodide paper by dipping strips of filter paper into a starch solution containing a small amount of iodide salt. Their solution is made by mixing 5 grams of soluble starch very thoroughly with a small amount of water to form a paste which is then added to 500 ml of boiling water. After cooling, 10 grams of potassium iodide are added. The strips of impregnated filter paper are drained and allowed to dry prior to use.

The purpose of the iodide is of particular interest here. "There should be present in the starch solution", the authors write, "at least 1 gram of potassium iodide per 100 ml to obtain a proper color with iodine, since the blue absorption compound contains iodide as well as iodine."

Indeed, the blue starch-iodine color is attributed to a continuous polyiodide chain spirally encased in a helical array of glucose units. The polyiodide chain itself is described as a rather complex stack of iodine ($I_2$) molecules interspersed with iodide ($I^-$) ions.

One of the novel aspects of the present invention stems from the nature of the solution used to treat the skin surface areas just prior to recording. It is a single solution that contains one solute serving two functions: (1) it is an iodine precursor, and (2) it is a source of iodide ions. No iodide is present in the paper of this invention as it would be unstable in the presence of the oxidizing agent contained therein. Thus, the starch-iodide paper used in iodometry and in analytical chemistry is substantially different from the product conceived by this invention. The iodometric test paper contains both starch and a small amount of a soluble iodide salt, but no oxidizer, while the paper of this invention contains starch and an oxidizing agent, but no iodide salt.

Further, in iodometry, free iodine is formed or consumed in the test solution, either directly or indirectly, as a result of an oxidation-reduction reaction. Iodine is not formed in the test paper itself but is generated externally. By contrast, in the present invention, free iodine is formed within the novel, coated or impregnated sheet material by a strong oxidizing agent contained therein. This oxidizer reacts in situ with iodide ions transported to the sheet surface by sweat gland moisture. A deep blue coloration is produced and the intensity of this imprint is enhanced, fortuitously, by the presence of both iodine and iodide species at the reaction site.

Figure 1:
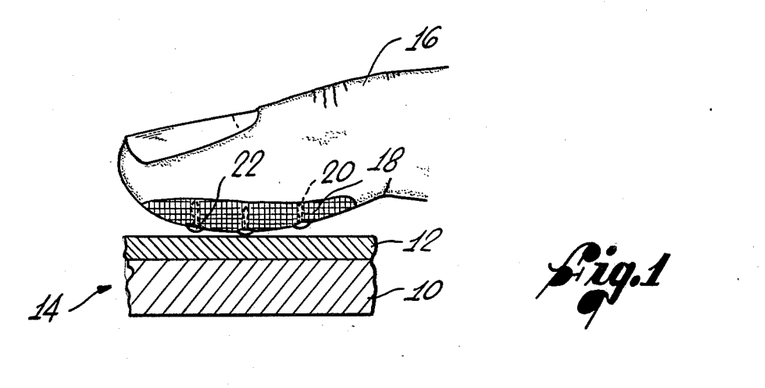
FIG. 1 is an enlarged sectional view of a means for recording sweat gland activity in accordance with the present invention.
Figure 2:
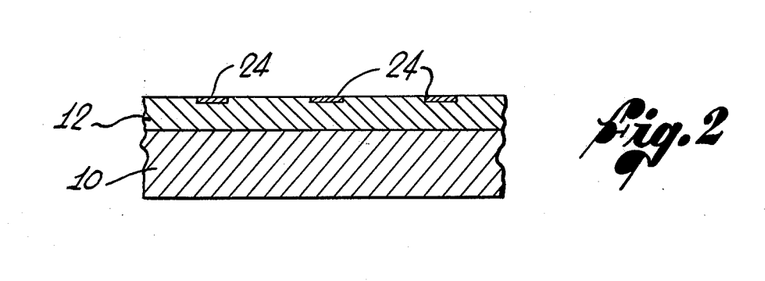
FIG. 2 is an enlarged sectional view of a dermatoglyph of sweat gland activity in accordance with the present invention showing an image formed as a result of sweat pore impression.

Referring now to the drawings and with reference to FIGS. 1 and 2, a suitable substrate 10, such as paper, film, foil or fabric, is coated with a light-colored sensitized layer 12 to form a sensitized substrate generally denoted as 14. The layer 12 comprises a mixture of starch and a suitable oxidizing agent. Of course, a suitable binder or an adhesive also may be included in the sensitized layer 12. However, since starch in itself is commonly used as a binder, no additional matrix material is needed.

In FIG. 1, a human thumb 16, treated with a colorless iodide solution 18 is depicted for recording purposes. Sweat glands 20, are shown diagrammatically to illustrate the normal exudation of droplets of perspiration 22. As the treated skin area 18 is pressed against the sensitized substrate 14, an image is formed by a dark starch-iodine reaction complex 24. In FIG. 2, the reaction complex 24, appears only in those areas where skin perspiration 22 carries the soluble iodide ions of the solution from the treated skin surface 18 to the sensitized layer 12. In those areas of the sensitized substrate where no transfer occurs, the substrate remains white, or light colored.

Figure 3:
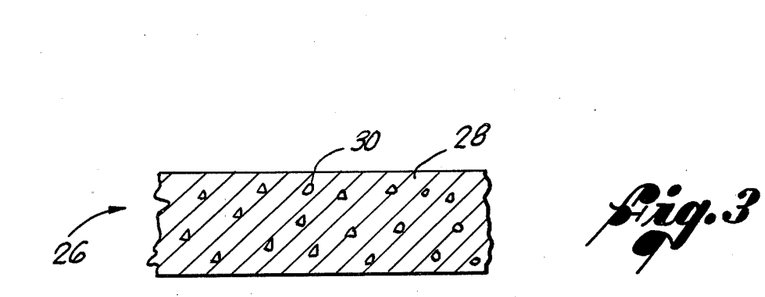
FIG. 3 is an enlarged sectional view of an alternative means for recording sweat gland activity in accordance with the present invention.

FIG. 3 depicts an alternate structure for the sensitized substrate generally denoted 26, wherein a saturating base 28 such as a heavy weight paper or fabric, is impregnated with a starch-iodizing agent mixture 30.

In one preferred embodiment of this invention, a suitable base paper is coated with an aqueous solution containing from 1 to 10 percent by weight of a high amylose starch, such as potato starch, "Mira-Quik C" corn starch (A. E. Staley Mfg. Company), or other suitable starch, and from 2 to 10 percent by weight of a water soluble oxidizing agent, such as sodium or potassium persulfate.

In preparing the coating mixture, the starch is preferably dissolved first. One acceptable method is mixing the starch with a small amount of cold water, diluting the slurry to the proper concentration, and then adding sufficient caustic such as NaOH, by stirring, to obtain a clear solution having a pH above 12. Other methods for solubilizing starches are known in the art and can vary from simple heating for a few minutes to cooking for an extended time period under pressure to produce a clear solution.

The starch solution is then cooled below about 75° C., and preferably to about 25° to 30° C. to prevent oxidative reaction of the starch when the oxidizing agent is subsequently added to the solution. This oxidative reaction is believed to take place at elevated temperatures among the many vicinal dihydroxy grounds present in the starch molecule.

Sodium and potassium persulfate salts are preferred as oxidizing agents in this invention because these salts have a very high reduction potential ($E° = 2.0$), they produce a white, or near-white coating, and their reduction product is a totally innocuous sulfate salt:

$$S_2O_8^{-2} + 2I^- \rightarrow I_2 + 2SO_4^{-2}$$

Other potassium and sodium salts, such as periodates, hypochlorites, hypobromates, and the like listed in Table I, do not perform as well in the context of this invention for various reasons. For instance, they adversely affect the shelf life of the sensitized substrate, or adversely affect the contrast and detail of the resultant dermatoglyph. However, oxidizing agents such as sodium persulfate, potassium persulfate, sodium iodate, sodium bromate, sodium chlorate and mixtures thereof have suitably performed in accordance with the method of this invention.

The cooled solution may be applied to the substrate by any one of a number of well known coating methods, such as wire-wound rod, air-knife, reverse-roll, dipping, spraying, brushing, and the like. The weight of the wet coating should be adjusted so as to give a dry substrate coverage in the range of 2 to 10 pounds per 3000 square feet, preferably about 4 to 6 pounds per 3000 square feet. After drying, the sensitized substrate is ready for use in accordance with the present method.

Alternately, the starch-oxidizer solution can be impregnated into the base substrate rather than coated onto the surface. For impregnating purposes, a more absorbent base substrate such as fabric or heavy weight or blotting paper is preferred. Typically, these base substrates are from about 2.5 mils to 5 mils in thickness having from about 2 to 10 pounds of impregnated solution per 3000 square feet.

Eight stock papers, listed in Table II, were selected for testing with 5%, 7.5%, 10% and 15% solutions of soluble starch and of potato starch saturated with $K_2S_2O_8$ at 25° Centigrade. From these results it became known that a pH factor was of major importance in determining the life and quality of the paper used. Further, it was determined that the type of base paper used will exhibit a marked effect on the shelf-life of the ultimately coated substrate.

Accordingly, prior to using the solution for coating or impregnation, its pH should be adjusted to a value depending upon the oxidizer being used. For the persulfates and for sodium iodate, a pH value of 7 or 8 has been found to produce the most intense and stable prints; for sodium chlorate, a pH value should be about 4 to 6.

The resultant solution can be used as prepared in accordance with the foregoing discussion, or certain other agents, such as surfactants, water soluble thickeners for example, carboxymethyl cellulose, buffers, or other additives to control viscosity, wetting properties and levelling characteristics, may also be included in the solution as required by the particular method used to apply the solution to the substrate. The use of these additives is well known in the art of coating and need not be reviewed here.

As a rule, the coating solution should be applied as soon as possible after mixing, preferably within a twelve hour period. Degradation can be seen in coatings made from solutions aged longer than this period.

Any appropriate substrate may be used in accordance with the principles of this invention, such as paper, film, foil, or fabric, provided the substrate is essentially inert with respect to the starch-oxidizer solution. In this connection, it has been found, for example, that with high wet strength papers, particularly those containing urea- or melamineformaldehyde resins, shelf life of the paper is greatly reduced. Although the exact reason is not fully understood, it is believed that the release of formaldehyde, a strong reducing agent, causes the oxidizer to be slowly consumed. When such paper is finally used for the dermatoglyphs, there is insufficient oxidizer available to convert the iodide ions present in the sweat droplets to free iodine, and only a faint image appears.

Thus, a non-wet strength paper is preferred for the purposes of this invention. Depending upon the curl tendency of the base paper, it may be desirable to apply the starch-oxidizer solution to one or both sides of the sheet. A two-sided coating provides a more balanced sheet with respect to curl and may have economic advantages as well.

Although either coated or uncoated base papers can be used, a smooth, coated grade is preferred because it provides better image resolution.

The skin area to be recorded by means of the dermatographic method of this invention must first be treated with the iodide solution. Sodium iodide, calcium iodide or potassium iodide solutions in water, or a lower alcohol, or a mixture of these liquids will perform acceptably. However, because rapid drying is essential to completing the process quickly, a methanol ethanol or propyl alcohols solvent is preferred.

An iodide solution containing from about 2 to 25 percent by weight of sodium iodide in methanol and preferably about 10 percent by weight in methanol, is used to treat the sweat gland area to be tested. After allowing about 10 to 30 seconds for drying, the skin area is pressed against the sensitized substrate. A contact time of from 5 to 120 seconds may be used depending upon ambient conditions and the type of print desired. A contact time of 1 minute is usually sufficient to produce good print density.

These and other considerations will be better understood from a review of the following examples:

EXAMPLE 1

7.5 parts by weight of potato starch was slurried in 87.5 parts of water. The slurry was heated to 85° C. to produce a clear solution. The starch solution was then cooled to 25° C. and 5.0 parts by weight of sodium persulfate ($Na_2S_2O_8$) was added to the solution.

The pH of this solution was adjusted to 8.0 by the dropwise addition of 2 N NaOH. The solution was then coated onto a sheet of coated, offset paper stock known as "60-pound Mountie Offset Opaque" produced by the Potlatch Corporation. The coating was applied by a hand drawdown method using a #30 wire wound coating rod (Mayer rod). The coating was air dried and found to weigh 4 pounds per 3000 square feet.

A palm print was made by swabbing a subject's hand with a 10 percent solution (by weight) of sodium iodide in methanol, allowing the hand to dry for 20 seconds, and then contacting the sheet with moderate pressure for one minute. The resultant dermatoglyph was dense and contained the finest pore details.

EXAMPLE 2

The coated paper prepared in Example 1 was placed into an oven and kept at 60° C. for 72 hours. This period of heat aging is believed to simulate about six months natural aging at room temperature. After the 72-hour accelerated aging period, a palm print was made in the same manner as Example 1. There was no significant difference in image density or clarity.

EXAMPLE 3

The procedures of Example 1 were repeated using a 5 percent by weight aqueous solution of "Mira-Quik C" corn starch instead of potato starch and was adjusted to a final pH of 10.0. The resultant dermatoglyph was slightly better in terms of image density and clarity.

EXAMPLE 4

The procedures of Example 1 were repeated using a 2 percent by weight aqueous solution of potato starch prepared at 85° C. Potassium persulfate ($K_2S_2O_8$) was added to the starch solution and a pH of 7.0 was attained by dropwise addition of 2 N NaOH. The resultant dermatoglyph was dense and contained fine pore details.

EXAMPLE 5

The procedures of Example 1 were repeated using a 2.5 percent by weight aqueous solution of "Mira Quick" high amylose starch having an initial pH of 13 at a temperature of 25° C. Sodium persulfate ($Na_2S_2O_8$) at a 10 percent by weight concentration was added as the oxidizing agent. A final pH of 7.0 was used for coating solution. Again, the resultant dermatoglyph was dense and contained fine pore details.

EXAMPLE 6

The procedures of Example 1 were repeated using a 2 percent by weight aqueous solution of potato starch and prepared at a temperature of about 80° C. 7.5 percent by weight of sodium persulfate was added as the oxidizing agent and the final pH value of the solution was adjusted to 7.0. The resultant dermatoglyph was dense and contained fine pore detail.

EXAMPLE 7

The procedures of Example 1 were repeated using a 2 percent by weight aqueous solution of "Mira Quick" high amylose starch at an initial pH value of 13 and prepared at a temperature of 25° C. 10 percent by weight of sodium persulfate ($Na_2S_2O_8$) was added as the oxidizing agent and the final pH value was adjusted to 7.0. The resultant dermatoglyph was dense and contained fine pore detail.

EXAMPLE 8

The procedures of Example 1 were repeated using a 2 percent by weight aqueous solution of "Mira Quick" high amylose starch at an initial pH of 13 and at a temperature of 90° C. 10 percent by weight of sodium persulfate ($Na_2S_2O_8$) was added as the oxidizing agent and a final pH value of 7.0 was attained. The resultant dermatoglyph was dense and contained fine pore detail.

EXAMPLE 9

The procedures of Example 1 were repeated using a 5 percent by weight aqueous solution of "Mira Quick" high amylose starch solution prepared at 100° C. (saturation time of 3 hours). 5 percent by weight of sodium persulfate ($Na_2S_2O_8$) was added as the oxidizing agent and a final pH value of 10.0 was attained. The resultant dermatoglyph contained excellent pore resolution and detail.

EXAMPLE 10

The procedures of Example 1 were repeated using a 5 percent by weight aqueous solution of potato starch prepared at 85° C. 5 percent by weight sodium persulfate was added as the oxidizing agent and a final pH value of 8.0 was attained. The resultant dermatoglyph was dense and contained fine pore detail.

EXAMPLE 11

The conditions of Example 1 were repeated using a 5 percent by weight aqueous solution of potato starch prepared at 85° C. 7.5 percent by weight of sodium persulfate was added as the oxidizing agent and a final pH of 8.0 was attained. The resultant dermatoglyph was dense and contained fine pore detail.

EXAMPLE 12

The conditions of Example 1 were repeated using a 10 percent by weight aqueous solution of potato starch prepared at 80° C. 5 percent by weight sodium persulfate was added as the oxidizing agent, and a pH of 8.0 was attained. The resultant dermatoglyph was dense and contained fine pore detail.

With slight modifications, the foregoing method and means for recording sweat gland activity can also be utilized as a system for producing inkless fingerprints. Accordingly, a quick drying starch-oxidizing agent coating solution is prepared comprising from about 1 to 10 percent by weight starch, 2 to 20 percent by weight of oxidizing agent and the remainder being a suitable solvent, preferably incorporating some alcohol. Alcohols such as ethanol and methanol are preferred for this purpose which give the coating solution, when applied, a more rapid penetration into the substrate. Further, the iodide solution applied to the skin area comprises 2 to 25 percent by weight of the aforementioned iodide compounds and a solvent, preferably including water so as to make the fingerprinting method relatively independent of sweat gland activity. Optionally, to prevent premature oxidation of the iodide solution, small quantities of anti-oxidants for example, from about 0.5 to 5.0 percent by weight of thiourea, catechol, sodium formaldehyde, bisulfite or other suitable anti-oxidants may be incorporated into the iodide solution. However, the amount of anti-oxidant agent added should not exceed a level that would prevent or diminish the ultimate starch-iodine reaction. Further, a light colored pigment can be added to the starch-oxidizing agent coating fluid in an amount of from about 1 to 10 percent by weight to improve contrast of the coating fluid when applied to relatively dark colored substrates such as bank checks, or other colored documents. Suitable pigments include inert clays or pigments such as calcium carbonate, zinc oxide or titanium dioxide.

In the starch-iodide fingerprinting method, the starch-oxidizing agent coating solution is applied to a suitable substrate and allowed to dry to provide a sensitized coating in situ. Accordingly, the skin area to be recorded is moistened with the use of the aqueous iodide solution and physically contacted with the dry sensitized coated area of the substrate while the skin area is still moist. A stamp moistening pad, sponge, tissue or other suitable applicator can be used for applying the sensitized coating solution to the substrate and the iodide solution to the skin area.

The following examples will illustrate the starch-iodide fingerprint embodiment in accordance with the present invention.

EXAMPLE 13

An iodide solution was prepared one using potassium iodide in a mixture of water and glycerol for the purposes of moistening the skin area to be recorded. A starch-oxidizing agent solution was prepared using a mixture of starch, water and potassium persulfate for producing an in situ sensitized coating fluid on a paper substrate. The iodide solution had the following composition: potassium iodide in an amount of about 35 grams, water in an amount of about 15 grams and glycerol in an amount of about 60 grams. More particularly, the iodide solution was prepared by adding the potassium iodide to the water with stirring and then adding the glycerol with continued stirring for about ten minutes. The iodide solution was then stored in a suitable reservoir.

The starch-oxidizing agent solution was prepared from potato starch in an amount of about 5 grams, water in an amount of about 90 grams and potassium persulfate in an amount of about 7.5 grams. A small quantity of water was first added to the dry starch and mixed to form a paste. A magnetic stirrer and hot plate were used to effect continued stirring while the rest of the water was added. The solution was brought to a boil and then removed from the heat and allowed to cool below about 80° F. Subsequently, the potassium persulfate was added with stirring and continued mixing for about ten minutes. This solution was also then contained in a suitable reservoir.

The starch-oxidizing agent coating solution was applied to the back of a bank check and allowed to dry to provide a sensitized coating in situ. Next, several fingertips were moistened with the iodide solution and contacted with the dry sensitized area of the bank check while the fingertips were still moist. Several fingerprints were produced showing excellent resolution and ridge pattern. However, upon continued exposure to air, the fingerprints became rather dark.

EXAMPLE 14

The iodide solution and starch-oxidizing agent solution of Example 13 were again prepared using the compositions described therein. However, the iodide solution was diluted with denatured alcohol (ethanol) in a 1:1 ratio yielding an iodide solution of about 16 percent by weight potassium iodide, 7 percent by weight water, 28 percent by weight glycerol and about 50 percent by weight denatured alcohol. Again, the starch-oxidizing agent coating solution was applied to a paper substrate and the iodide solution was applied to several fingertips. The resulting fingerprints were of excellent clarity and did not have the loss in density that was experienced with the batch prepared in Example 13.

It will be apparent from the foregoing that, while particular forms of the invention have been illustrated and described, various modifications can be made without departing from the spirit and scope of the invention. Accordingly, it is not intended that the invention be limited, except as by the appended claims.

We claim:

1. A method for recording sweat gland activity by obtaining a clear resolute image which is directly proportional to the amount of perspiration exuded at each sweat gland orifice, the method comprising the steps of:
   (a) providing a dry sensitized substrate having a surface layer comprising a mixture of a starch and an oxidizing agent;
   (b) treating a skin area to be recorded with an iodide solution of a compound selected from the group consisting of sodium iodide, calcium iodide, potassium iodide and mixtures thereof;
   (c) allowing the iodide treated skin area to dry in areas where no perspiration exists and to receive perspiration where it develops at each gland orifice; and
   (d) momentarily contacting the surface layer of the sensitized substrate with the iodide treated skin area to produce the clear resolute image.

2. The method of claim 1 wherein the dry sensitized substrate comprises a sheet material coated with a solution of a starch and an oxidizing agent.

3. The method of claim 2 wherein the dry sensitized substrate has a dry coating coverage of from about 2 to 10 pounds per 3000 square feet.

4. The method of claim 2 wherein the sheet material is paper.

5. The method of claim 2 wherein the sheet material is a polymeric film.

6. The method of claim 2 wherein the sheet material is a metallic foil.

7. The method of claim 2 wherein the sheet material is a fabric.

8. The method of claim 2 wherein the sheet material is a non-wet strength paper.

9. The method of claim 2 wherein the dry sensitized substrate is coated on both sides of the sheet material.

10. The method of claim 1 wherein the dry sensitized substrate comprises an absorbent base layer impregnated with the mixture of a starch and an oxidizing agent.

11. The method of claim 1 wherein the dry sensitized substrate comprises a sheet material coated with a solution containing from about 1 to 10 percent by weight of a starch, from about 2 to 10 percent by weight of an oxidizing agent and a solvent.

12. The method of claim 11 wherein the solution further includes an effective amount of surfactants.

13. The method of claim 11 wherein the solution further includes an effective amount of water soluble thickeners.

14. The method of claim 13 wherein said water soluble thickeners are selected from the group consisting of carboxymethyl cellulose, buffers and mixtures thereof.

15. The method of claim 1 wherein the dry sensitized substrate comprises an absorbent base layer impregnated with a solution containing from about 1 to 10 percent by weight of a starch, from about 2 to 10 percent by weight of an oxidizing agent and a solvent.

16. The method of claim 15 wherein the solution further includes an effective amount of surfactants.

17. The method of claim 15 wherein the solution further includes an effective amount of water soluble thickeners.

18. The method of claim 17 wherein said water soluble thickeners are selected from the group consisting of carboxymethyl cellulose, buffers and mixtures thereof.

19. The method of claim 1 wherein the amylose content of the starch is from about 20 to 55 percent by weight.

20. The method of claim 1 wherein the starch is selected from the group consisting of rice starch, corn starch, potato starch, wheat starch, tapioca starch and mixtures thereof.

21. The method of claim 1 wherein the oxidizing agent is selected from the group consisting of sodium persulfate, potassium persulfate, sodium iodate, sodium bromate, sodium chlorate, and mixtures thereof.

22. The method of claim 1 wherein the iodide solution comprises from about 2 to 25 percent by weight of sodium iodide in a solvent.

23. The method of claim 22 wherein said solvent is a lower alcohol.

24. The method of claim 23 wherein said lower alcohol is selected from the group consisting of methanol, ethanol, propyl alcohols and mixtures thereof.

25. The method of claim 1 wherein the iodide solution comprises from about 2 to 25 percent by weight of potassium iodide in a solvent.

26. The method of claim 25 wherein said solvent is a lower alcohol.

27. The method of claim 26 wherein said lower alcohol is selected from the group consisting of methanol, ethanol, propyl alcohols and mixtures thereof.

28. The method of claim 1 wherein the step of momentarily contacting the sensitized substrate is effected within a contact time from about 5 to 120 seconds.

29. The method of claim 1 wherein the dry sensitized substrate comprises a sheet material coated with a solution consisting essentially of from about 1 to 10 percent by weight of a starch selected from the group consisting of rice starch, corn starch, potato starch, wheat starch, tapioca starch and mixtures thereof, from about 2 to 10 percent by weight of an oxidizing agent selected from the group consisting of sodium persulfate, potassium persulfate, sodium iodate, sodium bromate, sodium chlorate, and mixtures thereof and remainder is a solvent.

30. The method of claim 1 wherein the dry sensitized substrate comprises an absorbent base layer impregnated with a solution consisting essentially of from about 1 to 10 percent by weight of a starch, selected from the group consisting of rice starch, corn starch, potato starch, wheat starch, tapioca starch and mixtures thereof, from 2 to 10 percent by weight of an oxidizing agent, selected from the group consisting of sodium persulfate, potassium persulfate, sodium iodate, sodium bromate, sodium chlorate, and mixtures thereof, and remainer is a solvent.

31. A means for recording sweat gland activity by obtaining a clear resolute image which is directly proportional to the amount of perspiration exuded at each sweat gland orifice, the means comprising in combination:
   (i) a dry sensitized substrate having a surface layer mixture of a starch and an oxidizing agent; and
   (ii) an iodide solution to be applied to a skin area to be recorded, the iodide solution of a compound selected from the group consisting of sodium iodide, calcium iodide, potassium iodide, and mixtures thereof and a solvent.

32. The means of claim 31 wherein the dry sensitized substrate comprises a sheet material coated with a solution of a starch and an oxidizing agent.

33. The means of claim 32 wherein the dry sensitized substrate has a dry coating coverage of from about 2 to 10 pounds per 3000 square feet.

34. The means of claim 32 wherein the sheet material is paper.

35. The means of claim 32 wherein the sheet material is a polymeric film.

36. The means of claim 32 wherein the sheet material is a metallic foil.

37. The means of claim 32 wherein the sheet material is a fabric.

38. The means of claim 32 wherein the sheet material is a non-wet strength paper.

39. The means of claim 32 wherein the dry sensitized substrate is coated on both sides of the sheet material.

40. The means of claim 31 wherein the dry sensitized substrate comprises an absorbent base layer impregnated with a mixture of a starch and an oxidizing agent.

41. The means of claim 31 wherein the dry sensitized substrate comprises a sheet material coated with a solution containing from about 1 to 10 percent by weight of a starch and from about 2 to 10 percent by weight of an oxidizing agent.

42. The means of claim 31 wherein the dry sensitized substrate comprises an absorbent base layer impregnated with a mixture containing from about 1 to 10 percent by weight of a starch and from about 2 to 10 percent by weight of an oxidizing agent.

43. The means of claim 31 wherein the starch has an amylose content of from about 20 to 55 percent by weight.

44. The means of claim 31 wherein the starch is selected from the group consisting of rice starch, corn starch, potato starch, wheat starch, tapioca starch and mixtures thereof.

45. The means of claim 31 wherein the oxidizing agent is selected from the group consisting of sodium persulfate, potassium persulfate, sodium iodate, sodium bromate, sodium chlorate, and mixtures thereof.

46. The means of claim 31 wherein the iodide solution comprises from about 2 to 25 percent by weight of sodium iodide in a solvent.

47. The means of claim 46 wherein said solvent is a lower alcohol.

48. The means of claim 47 wherein said lower alcohol is selected from the group consisting of methanol, ethanol, propyl alcohols and mixtures thereof.

49. The means of claim 31 wherein the iodide solution comprises from about 2 to 25 percent by weight of potassium iodide in a solvent.

50. The means of claim 49 wherein said solvent is a lower alcohol.

51. The means of claim 50 wherein said lower alcohol is selected from the group consisting of methanol, ethanol, propyl alcohols and mixtures thereof.

52. The means of claim 31 wherein the dry sensitized substrate comprises a sheet material coated with a solution consisting essentially from about 1 to 10 percent by weight of a starch, selected from the group consisting of rice starch, corn starch, potato starch, wheat starch, tapioca starch and mixtures thereof, and from about 2 to 10 percent by weight of an oxidizing agent, selected from the group consisting of sodium persulfate, potassium persulfate, sodium iodate, sodium bromate, sodium chlorate, and mixtures thereof, and remainder is a solvent.

53. The means of claim 31 wherein the dry sensitized substrate comprises a absorbent base layer impregnated with the mixture consisting essentially of from 1 to 10 percent by weight of a starch selected from the group consisting of rice starch, corn starch, potato starch, wheat starch, tapioca starch and mixtures thereof, and from 2 to 10 percent by weight of an oxidizing agent, selected from the group consisting of sodium persulfate, potassium persulfate, sodium iodate, sodium bromate, sodium chlorate, and mixtures thereof, and remainder is a solvent.

54. A method for producing a relatively permanent inkless fingerprint, the method comprising the steps of:
(a) providing a dry sensitized substrate having a surface layer comprising a mixture of starch and an oxidizing agent;
(b) moistening a skin area to be imprinted with an aqueous iodide solution of a compound selected from the group consisting of sodium iodide, calcium iodide, potassium iodide and mixtures thereof; and
(c) momentarily contacting the surface layer of the sensitized substrate with the iodide treated skin area, while said skin area is still in a moistened condition to produce the inkless fingerprint.

55. The method of claim 54 wherein the dry sensitized substrate comprises a sheet material coated with a solution of a starch and an oxidizing agent.

56. The method of claim 55 wherein the dry sensitized substrate has a dry coating coverage of from about 2 to 10 pounds per 3000 square feet.

57. The method of claim 55 wherein the sheet material is paper.

58. The method of claim 55 wherein the sheet material is a polymeric film.

59. The method of claim 55 wherein the sheet material is a metallic foil.

60. The method of claim 55 wherein the sheet material is a fabric.

61. The method of claim 55 wherein the sheet material is a non-wet strength paper.

62. The method of claim 55 wherein the dry sensitized substrate is coated on both sides of the sheet material.

63. The method of claim 54 wherein the dry sensitized substrate comprises an absorbent base layer impregnated with the mixture of a starch and an oxidizing agent.

64. The method of claim 54 wherein the dry sensitized substrate comprises a sheet material coated with a solution containing from about 1 to 10 percent by weight of a starch and from about 2 to 10 percent by weight of an oxidizing agent.

65. The method of claim 54 wherein the dry sensitized substrate comprises an absorbent base layer impregnated with a solution containing from about 1 to 10 percent by weight of a starch and from about 2 to 10 percent by weight of an oxidizing agent.

66. The method of claim 54 wherein the starch has an amylose content of from about 20 to 55 percent by weight.

67. The method of claim 54 wherein the starch is selected from the group consisting of rice starch, corn starch, potato starch, wheat starch, tapioca starch and mixtures thereof.

68. The method of claim 54 wherein the oxidizing agent is selected from the group consisting of sodium persulfate, potassium persulfate, sodium iodate, sodium bromate, sodium chlorate, and mixtures thereof.

69. The method of claim 54 wherein the aqueous iodide solution comprises from about 16 percent by weight of the iodide compound, about 7 percent by weight water, about 28 percent by weight glycerol and about 50 percent by weight alcohol.

70. The method of claim 54 wherein the aqueous iodide solution comprises from about 2 to about 25 percent by weight of the iodide compound in a solvent.

71. The method of claim 70 wherein said solvent is water.

72. The method of claim 54 wherein the step of momentarily contacting the sensitized substrate is effected within a contact time from about 5 to 120 seconds.

73. The method of claim 54 wherein the dry sensitized substrate is formed in situ by applying a sensitizing coating fluid comprising a solution of starch and an oxidizing agent to the surface of a substrate, and allowing the sensitizing fluid to dry.

74. The method of claim 54 wherein the dry sensitized substrate comprises a sheet material coated with a solution consisting essentially of from about 1 to 10 percent by weight of a starch selected from the group consisting of rice starch, corn starch, potato starch, wheat starch, tapioca starch and mixtures thereof, and from about 2 to 10 percent by weight of an oxidizing agent, selected from the group consisting of sodium persulfate, potassium persulfate, sodium iodate, sodium bromate, sodium chlorate, and mixtures thereof, and remainder is a solvent.

75. The method of claim 54 wherein the dry sensitized substrate comprises an absorbent base layer impregnated with a solution consisting essentially of from about 1 to 10 percent by weight of a starch selelcted from the group consisting of rice starch, corn starch, potato starch, wheat starch, tapioca starch and mixtures thereof, and from about 2 to 10 percent by weight of an oxidizing agent, selected from the group consisting sodium persulfate, potassium persulfate, sodium iodate, sodium bromate, sodium chlorate, and mixtures thereof and remainder is a solvent.

76. A sensitized substrate comprising a substrate having a surface layer with dry coating coverage of from about 2 to 10 pounds per 3,000 square feet, the surface layer including a mixture of a strach and an oxidizing agent, said starch being selected from the group consisting of rice starch, potato starch, corn starch, wheat starch, tapioca starch and mixtures thereof, and said oxidizing agent being selected from the group consisting of sodium persulfate, postassium persulfate, sodium iodate, sodium bromate, sodium chlorate, and mixtures thereof.

77. The sensitized substrate of claim 76 wherein the substrate comprises a sheet material coated with a solution of the starch, the oxidizing agent and a solvent.

78. The sensitized substrate of claim 77 wherein the sheet material is paper.

79. The sensitized substrate of claim 77 wherein the sheet material is a polymeric film.

80. The sensitized substrate of claim 77 wherein the sheet material is a metallic foil.

81. The sensitized substrate of claim 77 wherein the sheet material is a fabric.

82. The sensitized substrate of claim 77 wherein the sheet material is a non-wet strength paper.

83. The sensitized substrate of claim 77 wherein the substrate is coated on both sides of the sheet material.

84. The sensitized substrate of claim 77 wherein the solution further includes an effective amount of surfactants.

85. The sensitized substrate of claim 77 wherein the solution further includes an effective amount of water soluble thickeners.

86. The sensitized substrate of claim 85 wherein said thickeners are selected from the group consisting of carboxymethyl cellulose, buffers and mixtures thereof.

87. The sensitized substrate of claim 76 wherein the substrate comprises an absorbent base layer impregnated with the mixture of the starch and the oxidizing agent.

88. The sensitized substrate of claim 87 wherein the substrate comprises an absorbent base layer impregnated with a mixture consisting essentially of from about 1 to 10 percent by weight of the starch, from about 2 to 10 percent by weight of the oxidizing agent, and remainder is a solvent.

89. The sensitized substrate of claim 76 wherein the substrate comprises a sheet material coated with a solution containing from about 1 to 10 percent by weight of the starch and from about 2 to 10 percent by weight of the oxidizing agent.

90. The sensitized substrate of claim 76 wherein the substrate comprises an absorbent base layer impregnated with a mixture containing from about 1 to 10 percent by weight of the starch and from about 2 to 10 percent by weight of the oxidizing agent.

91. The sensitized substrate of claim 76 wherein the starch has an amylose content of from about 20 to 55 percent by weight.

92. The sensitized substrate of claim 76 wherein the substrate comprises a sheet material coated with a solution consisting essentially of from about 1 to 10 percent by weight of the starch, from about 2 to 10 percent by weight of the oxidizing agent and remainder is a solvent.

93. A sensitizing coating fluid comprising a starch, an oxidizing agent, and a solvent, said starch being selected from the group consisting of rice starch, corn starch, potato starch, wheat starch, tapioca starch and mixtures thereof, said oxidizing agent being selected from the group consisting of sodium persulfate, potassium persulfate, sodium iodate, sodium bromate, sodium chlorate and mixtures thereof, and said solvent being selected from the group consisting of alcohol, water, and mixtures thereof.

94. The sensitizing coating fluid of claim 93 wherein said starch is present in an amount of from about 1 to 10 percent by weight, and said oxidizing agent is present in an amount of from about 2 to 10 percent by weight and said solvent.

95. The sensitizing coating fluid of claim 93, wherein the starch has an amylose content of from about 20 to 55 percent by weight.

96. The sensitizing coating fluid of claim 93 wherein the solvent is methanol.

97. The sensitizing coating fluid of claim 93 wherein the solvent is ethanol.

98. The sensitizing coating fluid of claim 93 and further including a pigment selected from the group consisting of calcium carbonate, zinc oxide, titanium dioxide and mixtures thereof.

99. The senitizing coating fluid of claim 93 wherein said coating fluid consisting essentially of said starch in an amount of from 1 to 10 percent by weight, said oxidizing agent in an amount from 2 to 10 percent by weight and remainder is said solvent.

* * * * *

UNITED STATES PATENT AND TRADEMARK OFFICE
CERTIFICATE OF CORRECTION

PATENT NO. : 4,190,056
DATED : 2/26/80
INVENTOR(S) : Tapper, et al

It is certified that error appears in the above-identified patent and that said Letters Patent are hereby corrected as shown below:

Column 14, line 20, "remainer" should read -- remainder --.

Column 15, line 35, "a absorbent" should read -- an absorbent --.

Column 16, line 67, "selelcted" should read -- selected --.

Column 17, line 10, "strach" should read -- starch --.

Column 17, line 41, "carboxmethyl" should read -- carboxymethyl --

Column 18, line 46, "senitizing" should read -- sensitizing --.

Signed and Sealed this

Tenth Day of June 1980

[SEAL]

Attest:

SIDNEY A. DIAMOND

Attesting Officer

Commissioner of Patents and Trademark